(12) United States Patent
Sampson et al.

(10) Patent No.: US 7,947,460 B2
(45) Date of Patent: May 24, 2011

(54) METHOD FOR DIAGNOSIS AND THERAPY OF HAZELNUT-INDUCED SYSTEMIC REACTION

(75) Inventors: Hugh A. Sampson, Larchmont, NY (US); Kirsten Beyer, Berlin (DE)

(73) Assignee: Mount Sinai School of Medicine, New York, NY (US)

( * ) Notice: Subject to any disclaimer, the term of this patent is extended or adjusted under 35 U.S.C. 154(b) by 800 days.

(21) Appl. No.: 10/859,034

(22) Filed: Jun. 2, 2004

(65) Prior Publication Data

US 2005/0048576 A1 Mar. 3, 2005

Related U.S. Application Data

(60) Provisional application No. 60/475,548, filed on Jun. 2, 2003.

(51) Int. Cl.
*G01N 33/53* (2006.01)
(52) U.S. Cl. ........................................................ 435/7.1
(58) Field of Classification Search .................. None
See application file for complete search history.

(56) References Cited

FOREIGN PATENT DOCUMENTS

EP 0 994 353 A1 4/2000

OTHER PUBLICATIONS http://www.scripps.edy/cgi-bin/cdputnam/protcalc3 'Amino Acids 1-320 of SEQ ID No. 2 of U.S. Appl. No. 10/859,034.'*

Blumenthal et al. 'Definition of an Allergen.' Allergens and Allergen Immunotherapy. Ed. R Lockey, S. Bukantz and J. Bousquet. New York: Marcel Decker, 2004. 37-50.*
Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994. 491-495.*
Skolnick et al. 'From genes to protein structure and function: novel applications of computational approaches in the genomic era.' Trends in Biotech. 18(1):34-39, 2000.*
Attwood TK. 'The Babel of Bioinformatics.' Science 290:471-473, 2000.*
Lerner et al. 'Tapping the immunological repertoire to produce antibodies of predetermined specificity.' Nature 299:59-596, 1982.*
Beyer et al. 'Identification of an 11S globulin as a major hazelnut food allergen in hazelnut-induced systemic reactions.' Allergy 57Suppl. 73):82, 2002.*
Meinkoth et al. 'Hybridization of nucleic acids immobilized on solid supports.' Anal. Biochem. 138:267-284, 1984.*
http://www.scripps.edy/cgi-bin/cdputnam/protcalc3 'Amino Acids 1-320 of SEQ ID No. 2 of U.S. Appl. No. 10/859,034.' May 2, 2007.*
European Patent Application EP 0 981050A1, Feb. 23, 2000.
Beyer et al. (2002) J. Allergy Clin. Immunol. 110:517-523.
Luttkopf et al. (2001) Molecular Immunology 38:515-525.
Pastorello et al. (2002) J. Allergy Clion. Immunol. 109:563-570.
Schocker et al. (2000) Eur. J. Nutr. 39:172-180.
Ortolani et al. (2000) *J. Allergy Clin. Immunol.* 105:577-581.
Schocker et al. (2004) *J. Allergy Clin. Immunol.* 113:141-147.
Wallowitz et al. (2004) *J. Allergy Clin. Immunol.* 113:5156.

* cited by examiner

*Primary Examiner* — Nora M Rooney
(74) *Attorney, Agent, or Firm* — Fox Rothschild LLP (57) ABSTRACT

The present invention is directed to methods for predicting or diagnosing a hazelnut-induced systemic reaction, and for methods for treating such a reaction.

16 Claims, 3 Drawing Sheets

Fig. 1

```
                                    M   A   K   L   I   L   V   S   F   S   L   C
   1 AAA CAA CAT CAG ATA TAT ATT ACC ATG GCC AAA CTT ATC TTG GTC TCT TTT TCT CTG TGC   60
     L   L   V   L   F   N   G   C   L   G   I   N   V   G   L   R   R   Q   Q   Q
  61 CTT CTT GTG CTC TTC AAT GGC TGC CTG GGT ATC AAT GTA GGA CTA AGG CGG CAG CAA CAG  120
     R   Y   F   G   E   X   N   L   D   R   L   N   A   L   E   P   T   N   R   I
 121 CGA TAT TTT GGC GAG TGC AAC CTC GAC AGG CTC AAT GCC CTT GAA CCC ACA AAC CGC ATC  180
     E   A   E   A   C   Q   I   E   S   W   D   H   N   D   Q   Q   F   Q   X   A
 171 GAG GCT GAA GCT TGC CAG ATC GAG TCT TGG GAC CAC AAC GAC CAG CAA TTC CAG TGC GCT  240
     G   V   A   V   I   R   R   T   I   E   P   N   G   L   L   L   P   Q   Y   S
 241 GGG GTT GCC GTC ATC CGG CGA ACC ATT GAG CCC AAT GGC CTT CTC TTG CCC CAA TAC AGC  300
     N   A   P   E   L   I   Y   I   E   R   G   R   G   I   T   G   V   L   F   P
 301 AAT GCT CCA GAA CTC ATA TAC ATT GAG AGA GGT AGG GGA ATC ACC GGG GTC CTG TTT CCT  360
     G   X   P   E   T   F   E   D   P   Q   Q   Q   S   Q   Q   G   Q   R   Q   G
 361 GGG TGT CCC GAA ACA TTT GAA GAT CCT CAA CAA CAA TCT CAA CAG GGA CAG AGA CAG GGA  420
     Q   G   Q   S   Q   R   S   E   Q   D   R   H   Q   K   I   R   H   F   R   E
 421 CAG GGA CAG AGC CAG AGG TCT GAA CAA GAC CGG CAT CAG AAG ATT CGA CAC TTC CGA GAG  480
     G   D   I   I   A   L   P   A   G   V   A   H   W   C   Y   N   D   G   D   S
 481 GGA GAC ATC ATC GCA TTG CCA GCT GGA GTA GCC CAT TGG TGC TAT AAC GAC GGT GAC TCC  540
     P   V   V   T   V   S   L   L   H   T   N   N   Y   A   N   Q   L   D   E   N
 541 CCA GTT GTC ACA GTC TCT CTC CTT CAC ACC AAC AAC TAT GCT AAC CAG CTT GAC GAG AAC  600
     P   R   X   X   X   X   X   X   X   X   X   X   X   X   X   X   X   X   X   X
 601 CCT AGA CAC TTC TAC CTT GCC GGG AAC CCA GAC GAC GAG CAT CAG CGA CAG GGT CAG CAG  660
     X   X   X   X   X   R   R   Q   Q   Q   H   S   H   G   E   Q   G   E   Q   E
 661 CAA TTC GGG CAG CGT CGC CGC CAG CAA CAG CAT AGC CAT GGT CAG CAA GGC CAG CAA GAG  720
     Q   Q   G   E   G   N   N   V   F   S   G   F   D   A   E   F   L   A   D   A
 721 CAG CAG GGC GAA GGA AAC AAC GTA TTC AGT GGC TTC GAT GCT GAG TTT TTG GCG GAC GCG  780
     F   N   V   D   V   D   T   A   R   R   L   Q   S   N   Q   D   K   R   R   N
 781 TTC AAC GTG GAT GTT GAC ACG GCC AGA AGG CTT CAG AGC AAC CAA GAC AAA AGG AGG AAC  840
     I   V   K   V   E   G   R   L   Q   V   V   R   P   E   R   S   R   Q   E   W
 841 ATC GTC AAA GTG GAA GGC AGG CTT CAG GTG GTG AGG CCG GAA AGG TCG CGT CAG GAA TGG  900
     E   R   Q   E   R   Q   E   R   E   S   E   Q   E   R   E   R   Q   R   R   Q
 901 GAG CGA CAG GAG AGA CAA GAG AGG GAG AGT GAG CAA GAG CGG GAA CGC CAG CGT CGC CAG  960
     G   G   R   G   R   D   V   N   G   F   E   E   T   I   X   S   L   R   L   R
 961 GGA GGA CGT GGA CGT GAT GTC AAT GGC TTT GAG GAG ACA ATA TGC AGC TTG AGG CTC AGG 1020
     E   N   I   C   T   R   S   R   A   D   I   Y   T   E   Q   V   G   R   I   N
1021 GAA AAC ATC TGC ACC CGC TCA CGC GCT GAC ATT TAC ACC GAA CAA GTC GGT CGC ATC AAC 1080
     T   V   N   S   N   T   L   P   V   L   R   W   L   Q   L   S   A   E   R   G
1081 ACC GTC AAC AGC AAC ACC CTC CCA GTC CTC CGC TGG CTC CAG CTC AGC GCT GAG AGA GGA 1140
     D   L   Q   R   E   G   L   Y   V   P   H   W   N   L   N   A   H   S   V   V
1141 GAT CTT CAA AGG GAG GGT CTA TAT GTA CCG CAC TGG AAC CTC AAT GCC CAC AGT GTG GTG 1200
     Y   A   I   R   G   R   A   R   V   Q   V   V   D   D   N   G   N   T   V   F
1201 TAT GCC ATA CGG GGT CGC GCC CGA GTT CAG GTG GTG GAC GAC AAC GGT AAC ACC GTG TTC 1260
     D   D   E   L   R   Q   G   Q   V   L   T   I   P   Q   N   F   A   V   A   K
1261 GAC GAT GAA CTT AGA CAG GGT CAG GTG TTG ACC ATC CCC CAG AAC TTC GCG GTG GCG AAA 1320
     R   A   E   S   E   G   F   E   W   V   A   F   K   T   N   D   N   A   Q   I
1321 CGG GCA GAG AGC GAG GGT TTC GAG TGG GTG GCC TTC AAG ACC AAC GAC AAC GCC CAA ATT 1380
     S   P   L   A   G   R   T   S   A   I   R   A   L   P   D   D   V   L   A   N
1381 AGT CCT CTT GCC GGA CGA ACC TCA GCC ATC AGG GCC TTG CCG GAC GAT GTC CTT GCC AAC 1440
     A   F   Q   I   S   R   E   E   A   R   R   L   K   Y   N   R   Q   E   T   T
1441 GCG TTT CAG ATT TCA AGG GAG GAA GCC AGG AGG CTG AAA TAC AAC AGG CAG GAG ACC ACC 1500
     L   V   R   S   S   R   S   S   S   E   R   K   R   R   S   E   S   E   G   R
1501 TTG GTT CGC TCA AGC AGG TCT TCA TCT GAG AGG AAG AGG AGG TCT GAG TCT GAG GGC AGA 1560
     A   E   A   *
1561 GCT GAA GCT TAA TTG AAG ATC AAA AAA TGC TAA TGT AAT GCG GCA CGT AGT TTT ATT TTG 1620
1621 TGG TTG CTA AGC TTA GGG TTT AGG GCC ATC ACT ATG CAA CAG TCC TTC CTA ACT AGT ATA 1680
1681 ATC TGA GTG TAA AAA TAC GCA CAA GGG CAA CCT TTA CTA CAA AGA ATA AAA GTG ACC GCT 1740
1741 TTT TCT AAA AAA AAA AAA AAA AAA AAA 1767
```

Fig. 2

Ara h 3:   237 GNIFSGFTPEFLEQA 251

Cor a 9:   238 NNVFSGFDAEFLADA 252

Fig. 3

METHOD FOR DIAGNOSIS AND THERAPY OF HAZELNUT-INDUCED SYSTEMIC REACTION

CROSS REFERENCE TO RELATED APPLICATION

This application claims the benefit of U.S. provisional Application No. 60/475,548 filed Jun. 2, 2003, the disclosure of which is incorporated herein by reference.

STATEMENT REGARDING FEDERALLY SPONSORED RESEARCH

This invention was made with government support under Grant Number MO1 RR-00071 awarded by the National Institutes of Health. The government may have certain rights in the invention.

BACKGROUND OF THE INVENTION

The present invention is directed to methods for predicting or diagnosing a hazelnut-induced systemic reaction, and to methods for preventing or treating such a reaction.

The leading causes of severe food-induced allergic reactions are allergies to peanuts and tree nuts. The prevalence rate for peanut allergy, tree nut allergy, or both is 1.1% in the US population; allergy to tree nuts alone is found in 0.5%. Sicherer et al. (1999) J. Allergy Clin. Immunol. 103:599. Hazelnuts (Corylus avellana) are among the common tree nuts that lead to allergic reactions. In Europe the estimated prevalence of hazelnut allergy is 0.1% to 0.5%. Groot et al. (1996) Allergy 51:712. Allergy to hazelnuts is often found in patients with tree pollen allergy. These patients usually present with oral allergy syndrome caused by cross-reactivity between tree pollen allergens and hazelnut proteins. It has been shown that proteins similar to Cor a 1, the major hazel pollen allergen, and hazel profilin are also expressed in hazelnut and explain the sensitivity to hazelnut in patients allergic to tree pollen. Hirschwehr et al. (1992) J. Allergy Clin. Immunol. 90:927. More recently, a Bet v 1-related major allergen from hazelnut, Cor a 1.0401, has been cloned, expressed, characterized, and compared with the homologue in hazel pollen, Cor a 1.01. Luttkopf et al. (2002) Mol. Immunol. 38:515. On the other hand, severe allergic reactions to hazelnuts are reported in patients without any association to tree pollen allergy. Ortolani et al. (2000) J. Allergy Clin. Immunol. 105:577. These patients usually have urticaria, angioedema, asthma, vomiting, pharyngeal edema, diarrhea, and/or anaphylaxis. Pastorello et al. (2002) J. Allergy Clin. Immunol 109:563 have identified a 9 kD protein in hazelnut that reacted with sera from seven patients with systemic reactions to hazelnut.

The world production of hazelnut has almost doubled in the last two decades, reaching greater than 600,000 tons of in-shell nuts. In the United States 99% of hazelnuts are grown in Oregon, and the main cultivars are Barcelona, occupying 80% of the plantations. Only 10% of the hazelnuts are eaten as in-shell nuts; the majority of the crop is cracked, and the kernels are sold to bakers, candy makers, and other processors. Hazelnuts are commonly found in chocolate, cakes, cookies, breakfast cereals, ice cream, pastries, breads, and confectionery products.

Despite the fact that hazelnuts are used increasingly in the United States and Europe and that allergic reactions are not limited to oral allergy syndrome through cross-reactivity with tree pollen allergens, the identification of hazelnut allergens is still incomplete. By using two-dimensional (2D) proteomics and Edman sequencing, followed by subsequent cloning and sequencing, a new major food allergen involved in the majority of non-tree pollen-associated hazelnut allergy has been identified in accordance with the present invention.

SUMMARY OF THE INVENTION

The present invention is directed to a hazelnut allergen useful for the diagnosis and treatment of hazelnut-induced systemic allergic reactions.

In one embodiment, the present invention provides an isolated nucleic acid that encodes Cor a 9, a subunit of Cor a 9, or a polypeptide or peptide comprising at least one epitope of Cor a 9. Expression vectors comprising the nucleic acids, and host cells comprising the expression vectors are also provided.

In another embodiment the invention provides a polypeptide or peptide comprising at least one epitope of Cor a 9. Fusion proteins comprising the polypeptide are also provided.

The present invention further provides a method of diagnosing or predicting hazelnut allergy comprising detecting antibodies against Cor a 9.

Another embodiment of the present invention provides a method of treatment of hazelnut allergy comprising administering a composition comprising a polypeptide of the invention to a mammal in need of such treatment.

BRIEF DESCRIPTION OF THE DRAWINGS

Molecular weight standards (MW) are shown on the left. The square marks the area recognized by serum IgE from 86% (12/14) of the patients with hazelnut allergy with systemic reactions. The arrow marks the 11S globulin-like protein that was identified as Cor a 9.

FIG. 2 depicts the nucleotide sequence (SEQ ID NO:1) of an 11S globulin cDNA clone and the deduced amino acid sequence (SEQ ID NO:2). The assumed cleavage site for the acidic and basic submits and the four conserved cysteine residues are marked by dark shading. The two peptides identified by Edman sequencing are marked by light shading.

DETAILED DESCRIPTION OF THE INVENTION

Allergic reactions to hazelnuts range from oral allergy syndrome, caused by cross-reactivity between birch tree pollen and hazelnut proteins, to systemic reactions including severe anaphylactic reactions. In accordance with the present invention, a hazelnut allergen has been identified that is highly predictive for a hazelnut allergy characterized by a systemic reaction.

The protein comprising the hazelnut allergen identified herein is an 11S globulin. The nucleotide (SEQ ID NO:1) and deduced amino acid (SEQ ID NO:2) sequences of a cDNA clone encoding the hazelnut 11S globulin are shown in FIG.

2. The nucleotide sequence has been submitted to the GenBank Database under accession number AF449424, and is disclosed in Beyer et al. (2002) J. Allergy Clin. Immunol. 110:517. The World Health Organization/International Union of Immunological Societies Allergen Nomenclature Subcommittee has designated the hazelnut 11S globulin-like protein of hazelnut as Cor a 9.

By alignment with other known 11S globulins it has been determined that the hazelnut 11S globulin discovered herein undergoes posttranslational modification with cleavage into an acidic and basic subunit linked by a disulfide bond. The acidic and basic subunits, asparaginyl cleavage site and conserved cysteine residues are depicted in FIG. 2.

Figure 3:
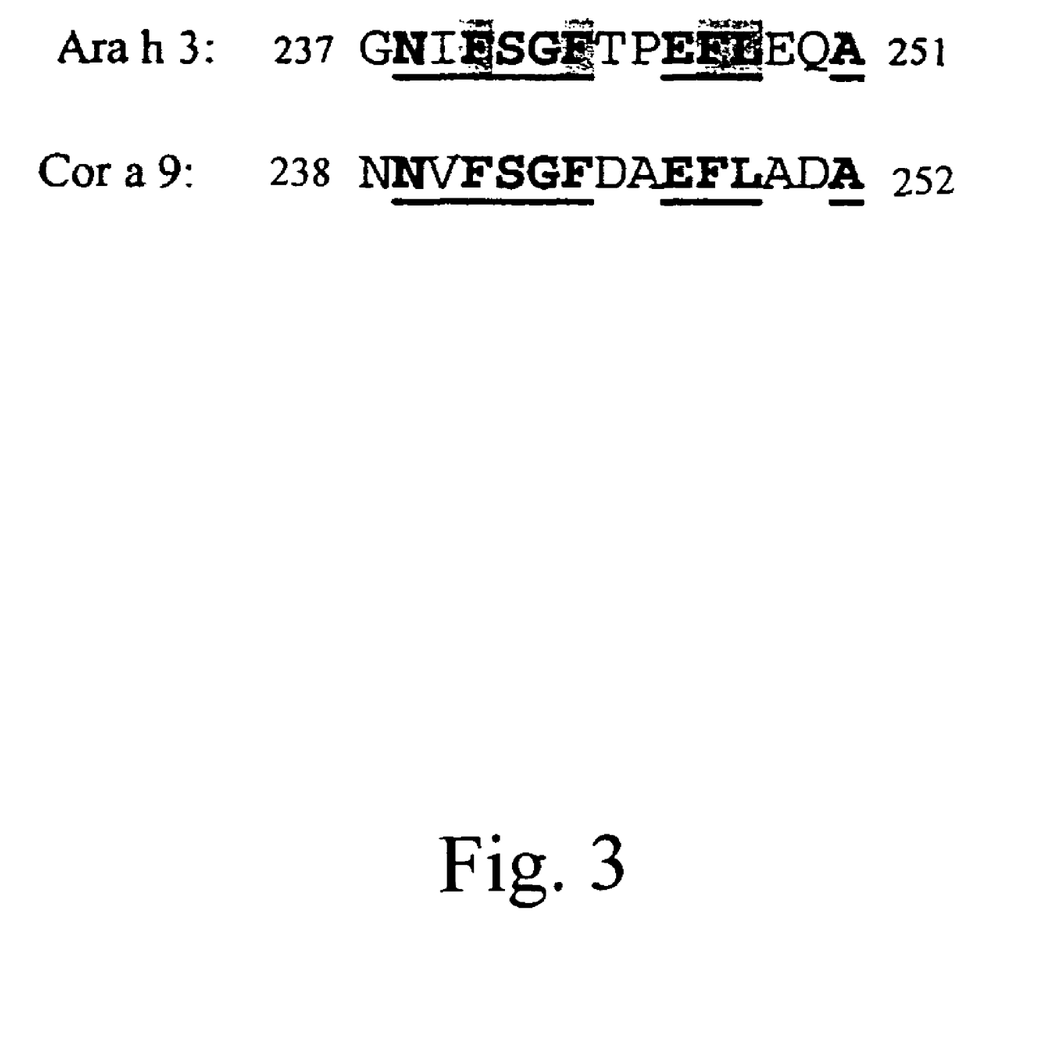
FIG. 3 shows the homology of amino acid sequences for peanut Ara h 3 and hazelnut Cor a 9 in the area of an IgE-binding epitope of Ara h 3. Identical amino acids are depicted in bold and underlined; homologous amino acids are underlined only. Amino acids that are highlighted in gray are known to lead to a loss of IgE-binding when substituted with another amino acid.

The acidic subunit encoded by nucleotides 25-924 of SEQ ID NO:1 and FIG. 2 is recognized by serum IgE from patients with hazelnut allergy characterized by systemic reactions, including some patients who had no specific IgE against hazel tree pollen, and including some patients whose serum did not recognize the hazelnut allergen Cor a 1.04. By homology to the peanut allergen Ara h 3, it has been determined that an IgE-binding epitope is present in Cor a 9 at amino acids 238-252 of SEQ ID NO:2 and FIG. 2 and has the sequence NNVFSGFDAEFLADA (SEQ ID NO:3). FIG. 3 shows amino acids that are identical to amino acids in the IgE-binding epitope of the peanut 11S globulin Ara h 3, including amino acids that are necessary for IgE binding.

The present invention provides isolated nucleic acids that encode Cor a 9. In one embodiment, the nucleic acid has the sequence of SEQ ID NO:1 and FIG. 2, and may be obtained as described herein from a hazelnut cDNA library. Degenerate variants of SEQ ID NO:1 that encode the polypeptide having the sequence of SEQ ID NO:2 are also included herein. In another embodiment, the nucleic acid is capable of hybridizing with a nucleic acid of SEQ ID NO:1, under high stringency conditions of 68° C. in aqueous buffered solution or 42° C. in 50% formamide, and encodes a polypeptide that is recognized by antibodies specific for Cor a 9.

The present invention also provides isolated nucleic acids that encode the acidic subunit of Cor a 9. In one embodiment the nucleic acid has the sequence of nucleotides 25-924 of SEQ ID NO:1. Degenerate variants encoding the polypeptide having the sequence of amino acids 1-320 of SEQ ID NO:2 are also contemplated. In another embodiment, the nucleic acid is capable of hybridizing with a nucleic acid having the sequence of nucleotides 25-924 of SEQ ID NO:1 under high stringency conditions as described above, and encodes a polypeptide that is recognized by antibodies specific for the acidic subunit of Cor a 9.

In another embodiment, the present invention provides isolated nucleic acids that encode the basic subunit of Cor a 9. In one embodiment the nucleic acid has the sequence of nucleotides 985-1569 of SEQ ID NO:1. Degenerate variants encoding the polypeptide having the sequence of amino acids 321-515 of SEQ ID NO:2 are also contemplated. In another embodiment, the nucleic acid is capable of hybridizing with a nucleic acid having the sequence of nucleotides 985-1569 of SEQ ID NO:1 under high stringency conditions, and encodes a polypeptide that is recognized by antibodies specific for the basic subunit of Cor a 9.

In another embodiment the present invention provides isolated nucleic acids that encode a polypeptide or peptide comprising at least one epitope of Cor a 9. Epitopes of Cor a 9 may be identified by providing a Cor a 9 epitope library and screening against serum from patients. Methods for creating and screening epitope libraries are known in the art and disclosed for example by Scott et al. (1990) Science 249:386. Epitopes may also be identified by computer algorithms and overlapping peptide synthesis technology, or by homology to IgE-binding epitopes of other nut or seed allergens. For example, a Cor a 9 epitope having SEQ ID NO:3 has been identified by homology to the IgE-binding epitope of Ara h 3 having the sequence GNIFSGFTPEFLEQA (SEQ ID NO:10). (FIG. 3). Identification of conserved residues with epitopes from other seed and nut allergens also allows a determination of residues that can tolerate substitution. Accordingly, variants of SEQ ID NO:3 and other epitopes that maintain IgE-binding ability are also included within the present invention.

The present invention further provides vectors comprising the isolated nucleic acids of the invention, host cells comprising the vectors, and polypeptides and peptides encoded by the nucleic acids.

The vectors are useful for the expression of the nucleic acids of the invention. In one embodiment, the vectors of the present invention comprise the nucleic acid operably linked to suitable transcriptional and/or translational regulatory elements to effect expression in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and are also commercially available. Recombinant viral vectors, including retrovirus, parvovirus, densovirus and baculovirus vectors are particularly preferred.

In a preferred embodiment, the expression vector comprises a strong constitutive or inducible promoter operatively linked to a nucleic acid of the invention. Suitable promoters are well known and readily available to one of ordinary skill in the art and include, for example, bacterial, yeast, viral, mammalian, and insect promoters. Expression vectors compatible with mammalian cells are particularly preferred.

Another embodiment of the present invention provides host cells comprising a nucleic acid of the invention. Host cells comprising the nucleic acid are useful for replicating and expressing the nucleic acids. The host cell may be prokaryotic or eucaryotic, including bacterial, yeast, insect or mammalian cells. Insect and mammalian cells are preferred.

The isolated nucleic acids or expression vectors may be introduced into the host cells by methods known to one of ordinary skill in the art, including transformation, transfection and infection. For example, transfection may be accomplished by known methods such as liposome mediated transfection, calcium phosphate mediated transfection, naked DNA transfection, microinjection and electroporation. Transformation methods of prokaryotic cells are described, for example, by Cohen et al. (1972) Proc. Natl. Acad. Sci. USA 69:2110. Transformation of eucaryotic host cells is described, for example, by Sambrook et al. (2000) Molecular Cloning: A Laboratory Manual, $3^{rd}$ edition, Cold Spring Press, Cold Spring Harbor, N.Y.

In another embodiment the present invention provides polypeptides and peptides comprising at least one epitope of Cor a 9. Isolated and purified polypeptides and peptides may be made by introducing a nucleic acid encoding the polypeptide or peptide into a suitable host cell, for example by transformation, transfection or injection, culturing the host cell under conditions suitable for expression, and recovering the recombinant polypeptide or peptide. The recombinant product may be recovered from cells or culture medium by methods known in the art. The polypeptides and peptides may also be made by well known methods of protein synthesis, such as solid phase peptide synthesis.

Biologically active analogs of the polypeptides and peptides are similarly made utilizing a nucleic acid encoding a biologically active analog. A biologically active analog is one which maintains the ability to be recognized by serum from patients having hazelnut-induced systemic reaction. The term "analogs" includes substitutions and alterations of the amino acid sequences described above, which substitutions and alterations maintain biological activity. Amino acid insertional derivatives include amino and carboxy terminal fusions and single or multiple intrasequence insertions. Deletional variants have one or more amino acids removed from the sequence. In substitutional amino acid variants, at least one residue has been removed or replaced by a different residue. The biologically active analogs may be made by recombinant methods as described for example by Sambrook et al. or by peptide synthetic techniques well-known in the art such as solid phase peptide synthesis.

Fusion proteins comprising the polypeptides and peptides of the present invention are also provided. The polypeptide or peptide may be fused, for example, to β-galactosidase or glutathione-S-transferase, or any other protein, for example to facilitate processing, purification or immobilization.

The present invention further provides compositions comprising a polypeptide or peptide comprising at least one epitope of Cor a 9. The compositions may further comprise a diluent, carrier, solubilizer, emulsifier, preservative and/or adjuvant.

In another embodiment, the present invention provides a method of diagnosing or predicting a hazelnut allergy characterized by a hazelnut-induced systemic reaction. The method comprises contacting an IgE-containing biological specimen of a mammal with a polypeptide or peptide of the invention, and detecting formation of a complex between an IgE in the specimen and the polypeptide or peptide of the invention. Detection of a complex is diagnostic of hazelnut allergy characterized by a systemic reaction. The biological specimen may be whole blood, sputum, serum, plasma, saliva, cerebrospinal fluid or urine. Preferably the sample is a blood, serum, or plasma sample obtained from a human subject.

Immunoassay formats using peptides or polypeptides to detect antibodies in a sample are well-known in the art and disclosed for example by Harlow and Lane (1988) Antibodies: A Laboratory Manual, Cold Spring Harbor Laboratory Press, Cold Spring Harbor, N.Y. In a preferred embodiment, the peptide or polypeptide is immobilized on a solid support to bind to the antibody and form a complex that is separated from the sample. The complex may be detected using a detection reagent that contains a reporter group, such as labeled anti-IgE. In a preferred embodiment, the assay is an enzyme linked immunosorbent assay (ELISA). Rapid flow through and test strip formats are also preferred. Competitive assays using labeled antibody may also be used.

Suitable solid supports are known in the art and include, for example, microtiter plates, nitrocellulose and other membranes, beads or discs such as glass, fiberglass, latex, polystyrene, polyvinylchloride, or magnetic particles. The polypeptides or peptides may be covalently or non-covalently attached to the support by methods known in the art.

The invention also provides kits useful for the detection of hazelnut allergy characterized by systemic reaction. The kits comprise one or more polypeptides or peptides of the invention, and an agent for detecting a complex of an antibody and the peptide or polypeptide. In a preferred embodiment, the peptide or polypeptide is immobilized.

In another embodiment, the present invention provides a method for treatment of a hazelnut allergy comprising administering a composition comprising a therapeutically effective amount of a polypeptide or peptide of the invention to a mammal in need of such treatment. In a preferred embodiment the mammal is a human. Such immunotherapeutic methods are known to those of ordinary skill in the art. A therapeutically effective amount of the polypeptide or peptide is defined herein as an amount effective to achieve hyposensitization.

The peptides and polypeptides are administered as a pharmaceutical composition containing the peptides or polypeptides and a pharmaceutically acceptable carrier.

The peptides and polypeptides may be modified and formulated for controlled delivery and for decreasing undesirable clinical reactions. Methods of modifying and formulating peptides and polypeptides for immunotherapy are known to those of ordinary skill in the art. For example, U.S. Patent Publication US 2003/0049237 A1, incorporated herein by reference, discloses methods of encapsulating antigens to reduce association of antigen with antigen-specific IgE antibodies, thereby reducing the risk of allergic reaction and possibly anaphylactic shock. U.S. Patent Publication US 2003/0049237 A1, incorporated herein by reference, discloses methods of modifying IgE binding sites of allergens to reduce allergenicity, for example by masking the IgE binding site or altering an amino acid within the protein. International Patent Publication WO 00/74716 A2 discloses various carriers for peptides, as well as peptide-based vaccines in the absence of protein carriers, and compositions comprising a plurality of allergy peptides linked by an inert carrier.

The formulation of pharmaceutical compositions is generally known in the art and reference can conveniently be made to Remington's Pharmaceutical Sciences, $17^{th}$ ed., Mack Publishing Co., Easton, Pa. Formulation for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms suitable for administration include sterile aqueous solutions or dispersions and sterile powders for the extemporaneous preparation of sterile injectable solutions or dispersions. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject polypeptides and peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The subject polypeptides and peptides are thus compounded for convenient and effective administration in pharmaceutically effective amounts with a suitable pharmaceutically acceptable carrier and/or diluent in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients. The use of such media and agents for pharmaceutical active substances is well known in the art. Supplementary active ingredients may also be incorporated into the compositions and used in the methods of present invention.

The precise therapeutically effective amount of the polypeptides or peptides, analogs or fragment thereof to be used in the methods of this invention applied to humans can be determined by the ordinary skilled artisan with consideration of individual differences in age, weight, extent of disease and condition of the patient.

It is especially advantageous to formulate parenteral compositions in dosage unit form for ease of administration and uniformity of dosage. Dosage unit forms as used herein refers to physically discrete units suited as unitary dosages for the mammalian subjects to be treated, each unit containing a predetermined quantity of active material calculated to produce the desired therapeutic effect in association with the required pharmaceutical carrier. The specification for the novel dosage unit forms of the invention are dictated by and directly depend on the unique characteristics of the active material, and the limitations inherent in the art of compounding such an active material for the treatment of hazelnut allergy.

The principal active ingredient is compounded for convenient and effective administration in effective amounts with a suitable pharmaceutically acceptable carrier in dosage unit form as hereinabove disclosed. In the case of compositions containing supplementary active ingredients, the dosages are determined by reference to the usual dose and manner of administration of the ingredients.

In the method of treatment according to the present invention, the polypeptides or peptides may be administered in a manner compatible with the dosage formulation, in such amount as will be therapeutically effective, and in any way which is medically acceptable for the treatment of hazelnut allergy. Possible administration routes include oral, nasal, transdermal and parenteral administration such as intravascular, intravenous, intraarterial, subcutaneous, intramuscular, intraperitoneal, intraventricular or intraepidural. Sustained release administration is also specifically included in the invention.

The peptides and polypeptides of the invention may also be used to generate antibodies. Such antibodies may be used as diagnostic and therapeutic agents, and include for example polyclonal, monoclonal, humanized and chimeric antibodies, single chain antibodies, antibody fragments, anti-idiotypic antibodies, and epitope-binding fragments of the foregoing antibodies. Methods of making such antibodies are known to those of ordinary skill in the art, and disclosed for example by Sambrook et al. (2000) supra and Harlow and Lane (1988) supra.

Antibodies raised against the peptides and polypeptides of the invention can be used to generate anti-idiotypic antibodies by methods known in the art, including for example Greenspan et al. (1993) FASEB. J., 7:437. Anti-idiotypic antibodies mimic the peptide and may be used for immunization. Compositions comprising the antibodies or anti-idiotypic antibodies and a carrier are also provided herein.

All references cited herein are incorporated herein by reference in their entirety.

The following nonlimiting examples serve to further illustrate the present invention.

Example 1

Methods

The following methods were used in subsequent examples.

Preparation of Hazelnut Extract

Hazelnuts were ground until a smooth paste was achieved by using a coffee grinder (Krups, Peoria, Ill.) followed by a mortar and pestle. The paste was defatted by means of washing with at least 20 volumes (wt/vol) of cold acetone and dried overnight at 4° C. Dried acetone powder was stored at −80° C. Protein was extracted from the defatted dried powdered pulp by agitating with PBS and a protease inhibitor cocktail without EDTA (Roche, Indianapolis, Ind.) overnight at 4° C. After centrifugation at 2500 g for 15 minutes at 4° C., the supernatant was collected, filtered, and centrifuged at 12,000 g for 3 minutes. Protein concentrations were determined by using the Coomassie Plus Protein Assay (Pierce, Rockford, Ill.). All extracts were stored at −80° C.

2D Proteomics Mapping

Crude hazelnut extract was suspended in Rehydration Buffer (9.8 mol/L urea, 4% Chaps, 2 mmol/L tributylphosphine, 0.2% Ampholytes, and 0.001% Bromophenol blue; Biorad, Hercules, Calif.) and applied to 7-cm immobilized pH 5-8 gradient strips (Biorad). After focusing for 17 hours with a linear voltage slope of up to 20,000 volt-hours, immobilized pH 5-8 gradient strips were equilibrated with urea, SDS, and glycerol containing Tris-HCl buffer in the presence of 5 mmol/L tributylphosphine for 10 minutes and then 135 mmol/L iodoacetamide for 10 minutes, followed by 2D gel electrophoresis with NuPAGE 4%-12% Bis-Tris ZOOM Gels (Invitrogen, Carlsbad, Calif.). The resolved proteins were subsequently transferred to Immobilon-P membrane (Millipore, Bedford, Mass.) and then stained with 2.2% Coomassie Blue for total protein analysis. For molecular weight determination, MultiMark Multi-Colored Standard (Invitrogen) was used.

Probing Immunoblots with Hazelnut-Sensitized Patient Sera

For detection of IgE binding to the separated hazelnut proteins, immunolabeling was performed with individual patient sera from 14 individuals with hazelnut allergy. The diagnosis of hazelnut allergy was based on clinical history and IgE measurement. Double-blind, placebo-controlled food challenges were not performed because of the severities of the systemic reactions. Clinical history and hazelnut-specific IgE levels detected with the Pharmacia FEIA-Cap System are shown in Table I.

TABLE I

Clinical reactions to hazelnut and to hazelnut- and hazel pollen-specific IgE for the 14 patients with hazelnut allergy

| Patient ID | Clinical reaction | Hazelnut IgE (kU/L) | Hazel pollen IgE (kU/L) | Pollen-related rhinoconjunctivitis | Recognition of 11S globulin |
|---|---|---|---|---|---|
| A | GI, urticaria | >100.00 | <0.35 | No | Yes |
| B | GI, resp | 15.8 | 4.78 | Yes | Yes |
| C | GI, urticaria | 6.33 | 13.5 | Unsure | Yes |
| D | OAS, angioedema, urticaria | 11.1 | 19.1 | No | Yes |
| E | Urticaria, resp | 8.44 | 37.7 | Yes | Yes |
| F | Urticaria, resp | 0.81 | <0.35 | No | Yes |
| G | Urticaria | 0.76 | 0.71 | No | Yes |
| H | Angioedema, resp | 0.93 | <0.35 | No | Yes |
| I | Resp | 1.1 | 8.25 | Yes | Yes |
| J | GI | 0.75 | <0.35 | No | No |
| K | Urticaria | 8.64 | <0.35 | No | Yes |
| L | GI | 2.51 | <0.35 | No | Yes |
| M | OAS, urticaria, resp | 3.78 | 0.57 | Yes | Yes |
| N | Urticaria, GI, resp | 12.7 | 4.8 | Unsure | No |

GI, Gastrointestinal symptoms; resp. respiratory symptoms; OAS, oral allergy syndrome.

In addition, reactions to other tree nuts, as well as peanuts, including the specific IgE levels against these foods, are shown in Table II.

TABLE II

Clinical reactions and specific IgE to other tree nuts and peanuts, as well as ages for the 14 patients with hazelnut allergy
Clinical reaction (specific IgE (kU/L) to:

| Patient ID | Peanut | Walnut | Brazil nut | Cashew nut | Almond | Age (y) |
|---|---|---|---|---|---|---|
| A | 0 (3.45) | NE (6.97) | NE (20.4) | NE (10.0) | NE (7.66) | 8 |
| B | 0 (53.5) | G, R, T (14.8) | NE (5.94) | G, R, T (19.1) | 0 (8.7) | 34 |
| C | G, U (>100) | G (6.93) | NE (4.48) | NE (88.4) | 0 (2.47) | 8 |
| D | A, T (>100) | NE (38.9) | NE (10.4) | NE (0.5) | NE (0.58) | 4 |
| E | NE (27.8) | NE (9.11) | NE (4.64) | U, R (4.45) | NE (6.51) | 6 |
| F | 0 (<0.35) | NE (<0.35) | NE (<0.35) | NE (37.0) | NE (<0.35) | 12 |
| G | 0 (1.24) | 0 (0.54) | NE (0.76) | U, T (7.53) | 0 (1.38) | 9 |
| H | 0 (<0.35) | G, A, R (0.79) | NE (1.09) | NE (1.04) | NE (0.87) | 2 |
| I | T (3.72) | NE (4.52) | NE (<0.35) | NE (<0.35) | 0 (<0.35) | 20 |
| J | 0 (<0.35) | U, A (7.45) | NE (<0.35) | 0 (<0.35) | 0 (<0.35) | 10 |
| K | NE (8.64) | NE (8.70) | NE (6.16) | NE (14.6) | NE (4.69) | 1 |
| L | 0 (0.65) | NE (<0.35) | NE (0.39) | NE (1.16) | NE (<0.35) | 2 |
| M | U, R, T (24.2) | G, R (15.8) | NE (1.13) | NE (28.0) | NE (0.6) | 11 |
| N | G (6.82) | G, U, R (31.2) | G, U, R (6.52) | G, U, R (24.5) | G, U, R 2.6 | 8 |

O, No reactions; NE, no known exposure, G, Gastrointestinal symptoms; R, respiratory symptoms; T, throat tightness; U, urticaria; A, angioedema.

Normal human serum (Pharmacia, Peapack, N.J.) was used as a negative control. Patient and control sera were diluted from 1:4 to 1:10 (depending on the level of hazelnut-specific IgE) in PBS-Tween plus 1% BSA and 10% normal goat serum and incubated with immunoblots for 1 hour by means of gentle agitation at room temperature. After brief rinsing with PBS, phosphatase-labeled goat anti-human IgE (KPL, Gaithersburg, Md.) at a concentration of 1 μg/mL goat IgG/mL in PBS-Tween plus 1% BSA and 10% normal goat serum was applied. After agitation for 45 minutes at room temperature and washing with PBS, followed by 50 mmol/L TRIS at pH 9.6, immunoblots were developed with phosphatase substrate BCIP/NBT (KPL). Protein images were analyzed with GelDoc 2000 (Biorad) by using Quantity One Quantitation Software.

MALDI MS Analysis and Edman Sequencing

According to the procedure described in the "2D Proteomics mapping" section, the hazelnut proteins were separated with 2D PAGE, and the gels were stained with Coomassie Blue. The protein at 40 kd was analyzed at the Wistar Institute Protein Microchemistry/Mass spectrometry Facility. Briefly, the spot was excised and digested with trypsin. The tryptic digests were separated by means of microbore HPLC, followed by MALDI MS analysis of selected peaks and subsequent Edman sequencing of 2 peaks by using standard methods.

Construction of a cDNA Library

A cDNA library was constructed from green Barcelona hazelnuts, which were a kind gift from Shawn Mehlenbacher from the Oregon State University. Total RNA was extracted according to the method of Chang et al, 1 (1993) Plant Mol. Biol. Reporter 11:113, and mRNA was purified on an Oligotex mRNA Spin column from Quiagen (Valencia, Calif.). Synthesis and cloning of cDNA was performed by using a cDNA synthesis kit from Stratagene (La Jolla, Calif.). The double-stranded cDNA was ligated into the lambda vector Uni-ZAP, packaged in vitro (Gigapak Gold, Statagene), and then transfected into *Escherichia coli* XL1-Blue cells.

Construction of 11S Globulin- and Cor a 1.04-Specific Primers, Screening of the cDNA Library, and Sequencing of Identified Clones The 11S globulin-specific primers were designed by using the 2 short amino acid sequences identified through Edman sequencing:

```
CAG/A GGI CAG/A CAG/A CAG/A       (SEQ ID NO: 4)
TTC/T GGI CAG/A and

CAC TTC TAC CTI GCT/C GGI AAC     (SEQ ID NO: 5)
CCA/T.
```

By using these primers, the cDNA library was screened, and the isolated clones were sequenced at the Mount Sinai Core Facility. In addition, the library was screened for Cor a 1.04. Two primers were designed by using the published sequence of this protein:

```
ATG AGG CCA CCT CCG TTA TC        (SEQ ID NO: 6)

and

GGA GGA GGA TCC ATC TTG AA        (SEQ ID NO: 7)
```

The sequenced clone was 100% identical to Cor a 1.0403 (GI:11762103).

Probing Identified Clones with Patient Sera

One of the isolated 11S globulin clones was incubated with *E coli* (strain Y 1090) for 15 minutes at 37° C. and plated in a layer of Luria-Bertani soft agar at a density of 100 plaques per plate. The plates were incubated for 5 hours at 42° C. After soaking in 10 nmol/L isopropyl thiogalactose, a Hybond C Extra membrane filter (Amersham Pharamacia Biotech, Piscataway, N.J.) was dried, placed on the agar plate, and further incubated overnight at 37° C. Then filters were preblocked in PBS-Tween plus 1% BSA and 10% normal goat serum for 1 hour. Individual sera from 2 patients who recognized the 11S globulin on the 2D gel were diluted 1:10 in PBS-Tween plus 1% BSA and 10% normal goat serum and incubated overnight at 4° C. with the filter. Iodine 125-labeled anti-human IgE (Diamed, Windham, Me.) diluted 1:5 was added after washing and incubated for 5 hours at room temperature. Filter was exposed to a X-OMAT film (Kodak, Rochester, N.Y.) with an intensifying screen at −20° C. for 24 to 48 hours and developed. Similar experiments were performed for Cor a 1.0403 for all 14 patients.

Example 2

Isolation, Cloning and Sequencing of Hazelnut Allergen

Proteins were separated by means of 2D gel electrophoresis and either stained with Coomassie Blue for total protein analysis or transferred to membranes and immunolabeled with sera from 14 individuals with hazelnut allergy to identify the major allergenic proteins of hazelnut. All individuals had systemic allergic reactions after consumption of hazelnut (Table I). Several of these patients were also sensitized against other tree nuts, peanuts, or both (Table II).

Figure 1:
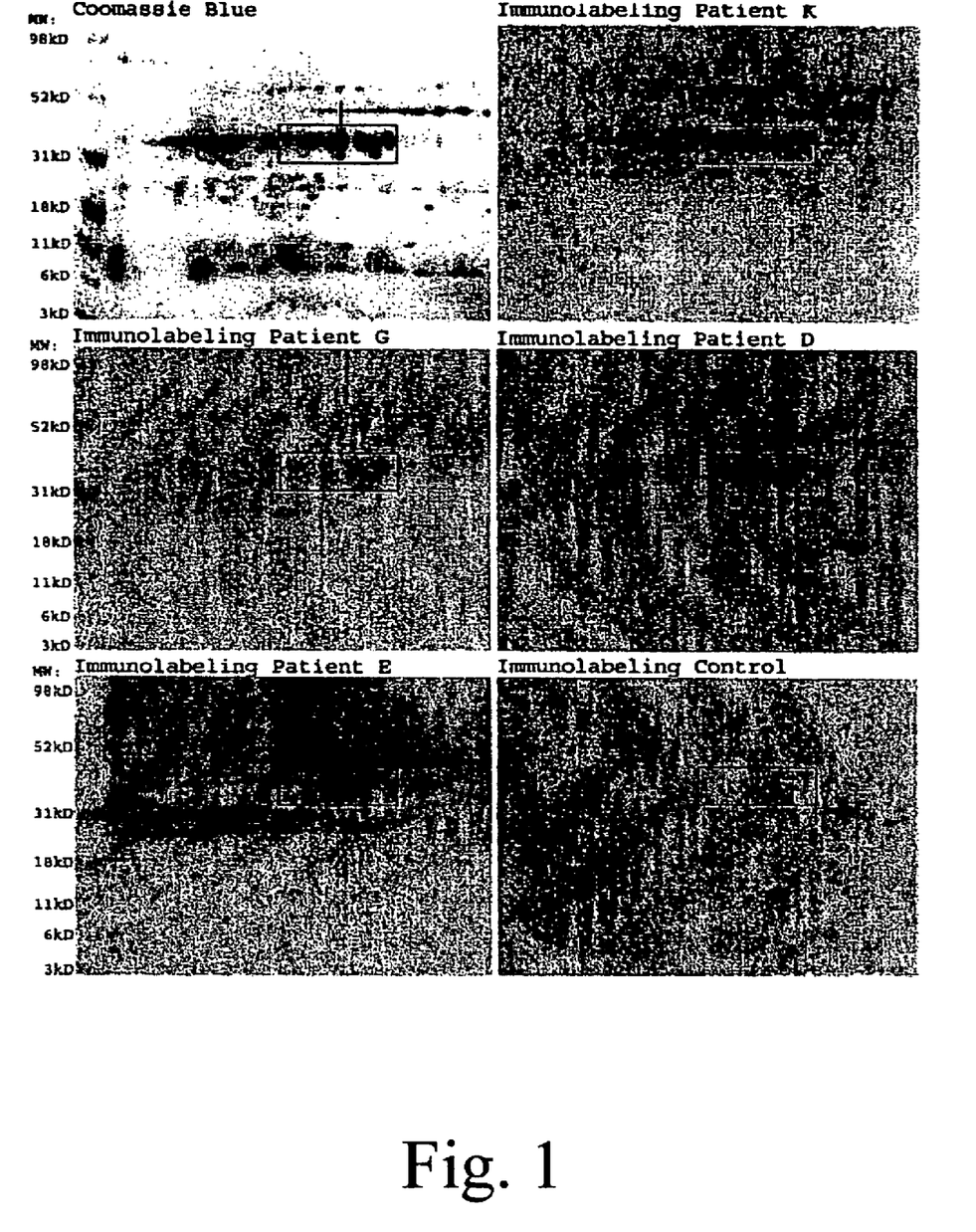
FIG. 1 is a two dimensional (2D) proteomics map for the water-soluble hazelnut proteins. Coomassie blue labeling for the total protein analysis and immunololabeling of sera from four representative patients and control serum are shown.

FIG. 1 shows the water-soluble hazelnut proteins separated by 2D PAGE. In addition to the Coomassie blue-stained membrane that shows all proteins, immunolabeling with sera from 4 representative patients and the negative control subject is presented. The IgE-binding pattern was quite different in all patients. However, several spots at 40 kd were recognized by sera from 12 of 14 patients with hazelnut allergy (FIG. 1 and Table I). To further analyze the spot at 40 kd, in-gel digestion and Edman sequencing was performed, and 2 internal sequences were obtained:

```
QGQQQFGQR                         (SEQ ID NO: 8)

and

HFYLAGNPDDEHQR.                   (SEQ ID NO: 9)
```

Through database screening, these sequences were shown to possess a significant homology to the legumin precursor of English oak and the pruning 2 precursor of almond, both of which are 11S globulin seed storage proteins. In parallel, RNA isolated from the Barcelona variety of hazelnuts was used to construct a cDNA library. The prepared cDNA library was screened with 2 phosphate 32-labeled oligonucleotides designed from the determined internal amino acid sequences to identify clones encoding the 11S globulin of hazelnut. The isolated clones were full-length sequenced. Analysis of the DNA sequence revealed that the obtained cDNA comprises an open reading frame of 1767 bp and encodes a 59-kd protein, apparently a precursor of the identified 40-kd polypeptide. The nucleotide sequence of the 11S globulin cDNA clone and the deduced amino acid sequence are shown in FIG. 2. The nucleotide sequence was submitted to the GenBank Database under accession number AF449424, and the World Health Organization/International Union of Immunological Societies Allergen Nomenclature Sub-Committee has designated the 11S globulin-like protein of hazelnut (*C. avellana*) as Cor a 9.

Furthermore, one of the identified clones was screened with individual sera from 2 of the patients with hazelnut allergy. Both patients showed IgE binding.

The 11S globulins described undergo posttranslational modification, with cleavage into 2 chains linked by a disulfide bond. The asparaginyl cleavage site that splits the Cor a 9 into the acidic and basic subunits, as well as the conserved cysteines involved in the disulfide bond between the subunits, were identified by alignment with other known 11S globulins from peanut (Ara h 3), soybean (glycinin), sesame, almond, and oak and highlighted in FIG. 2. The present protein on the 2D gel had a molecular weight of 40 kd and appears to be the acidic subunit of the protein cleaved under the reducing conditions of the gel electrophoresis (FIGS. 1 and 2).

Cor a 1.04 was previously described as a major allergen in hazelnut. A clone encoding Cor a 1.04 was also isolated from the cDNA library to clarify the role of Cor a 1.04 and Cor a 9 in the patients from the present study. The isolated clone was full-length sequenced and showed 100% identity with Cor a 1.0403. Screening with individual sera from all 14 patients with hazelnut allergy showed IgE binding in 7 (50%) of 14 patients.

This example demonstrates the identification of an 11S globulin as a major food allergen for hazelnuts. 11S Globulins belong to the family of seed storage proteins. Seed storage proteins have been known to be allergenic for many decades. They are divided into albumins and globulins. Albumins are water soluble at low salt concentrations, and globulins are water soluble at high salt concentrations.

The newly identified 11S globulin protein from hazelnut has been classified as a new major food allergen, Cor a 9. Thus far, 2 hazelnut allergens have been identified, Cor a 1, Breiteneder et al. (1993) Eur. J. Biochem. 212:355 and Cor a 8, a lipid transfer protein (accession no. AF329829). All allergens from the order Fagales (alder, birch, hornbeam, chestnut, hazel, and white oak) are considered to belong to one group of homologous proteins. Therefore, the number 9 has been assigned to the new allergen, regardless of whether it is a food allergen, a pollen allergen, or both.

11S Globulin seed storage protein from peanut (Ara h 3) and soybean (glycinin) have previously been identified as allergens. Looking at the entire sequence, the pairwise homology among these 3 proteins ranges from 45% to 50% (36%-41% identity), with the newly identified Cor a 9 having 49% homology with Ara h 3 and 50% with glycinin.

The 11S globulins are nonglycosylated proteins that form hexameric structures. This family represents the precursor protein, which is cleaved into 2 chains. Both chains are linked together by disulphide bonds. The protein identified on the 2D gel had a molecular weight of 40 kd and is the acidic subunit of the protein, dissociated from the smaller subunit under the reducing conditions of the gel electrophoresis. Similar to Cor a 9, binding of IgE from individuals with soy allergy has been found to soybean glycinin acidic chains. Pedersen (1989) Food Agric. Immunol. 1:101. In parallel, the majority of the IgE-binding sites of the glycinin G2 correspond to the acidic chain of the protein. Helm (2000) Int. Arc Allerg Immunol. 123:205. Similar results were found with regard to the peanut Ara h 3. All 4 identified B-cell epitopes, Rabjohn et al. (1999) 103:535, are located within the acidic chain.

In the present example 86% of patients with systemic reactions after the ingestion of hazelnuts recognized the hazel pollen-unrelated Cor a 9. Of these patients, 42% had no specific IgE against hazel pollen and did not present with pollen-related rhinoconjunctivitis, whereas the other might also recognize cross-reacting allergens. In addition, only 50% of the patient population of the present study recognize Cor a 1.04, another hazelnut allergen, indicating that Cor a 9 is the major hazelnut allergen for several individuals.

Pastorello et al (2002) J. Allergy Clin. Immunol. 109:563 identified 4 major allergens at 18, 32, 35, and 47 kd in hazelnut-sensitized patients with positive double-blind, placebo-controlled food challenge results. All of these patients presented with oral allergy syndrome, but 8 had gastrointestinal or mild systemic symptoms also. By using the partial N-terminal sequence, the 35-kd protein was further identified as a protein belonging to the legumin family, with 67% similarity to *Calocedrus decurrens*, a species of conifer. Comparing this N-terminal sequence with Cor a 9 showed a 99% homology.

Some individuals have clinical reactions to only one nut or seed whereas others react to several. Peanuts and tree nuts, as well as peanuts and seeds or tree nuts and seeds, are not closely related botanically. One of the 4 known IgE-binding epitopes of Ara h 3 has 67% identity with the corresponding area of Cor a 9 (FIG. 3). This epitope on Ara h 3 was recognized in previous studies by 38% of the study population. Rabjohn et al. (1999) J. Clin. Invest. 103:535. The different amino acids were previously shown not to be critical for IgE binding in Ara h 3 (FIG. 3).

The hazelnuts used in the present study were Barcelona hazelnuts from Oregon in the United States. By using SDS-PAGE and silver staining, it was shown previously that the protein patterns of different hazelnut varieties are quite similar. Mueller et al. (2000) Eur. Food Res. Technol. 212:2.

We claim:

1. A method of diagnosing a hazelnut allergy characterized by a hazelnut-induced systemic reaction comprising: contacting an IgE-containing biological specimen of a human with an isolated and purified polypeptide that forms a complex with serum IgE from a human with said allergy, wherein said polypeptide is encoded by a first nucleic acid having the sequence of nucleotides 25-924 of SEQ ID NO:1 or a second nucleic acid that hybridizes over the full length of the complement of said first nucleic acid under high stringency conditions comprising 68° C. in aqueous buffered solution and wherein said second nucleic acid encodes a polypeptide that is recognized by antibodies specific for the polypeptide encoded by said first nucleic acid; determining the presence or absence of a complex between IgE in the specimen and the polypeptide; and diagnosing hazelnut allergy characterized by a hazelnut-induced systemic reaction if the complex is present.

2. A method of diagnosing a hazelnut allergy characterized by a hazelnut-induced systemic reaction comprising: contacting an IgE-containing biological specimen of a human with an isolated and purified polypeptide that comprises the amino acid sequence of SEQ ID NO:2; determining the presence or absence of a complex between IgE in the specimen and the polypeptide; and diagnosing hazelnut allergy characterized by a hazelnut-induced systemic reaction if the complex is present.

3. The method of claim 1 wherein the biological specimen is whole blood, sputum, serum, plasma, cerebrospinal fluid or urine.

4. The method of claim 1 wherein the presence of the complex is determined by an immunoassay.

5. The method of claim 4 wherein the polypeptide is immobilized on a solid support.

6. A method of diagnosing a hazelnut allergy characterized by a hazelnut-induced systemic reaction comprising: contacting an IgE-containing biological specimen of a human with an isolated and purified polypeptide that comprises amino acids 1-320 of SEQ ID NO:2; determining the presence or absence of a complex between IgE in the specimen and the polypeptide; and diagnosing hazelnut allergy characterized by a hazelnut-induced systemic reaction if the complex is present.

7. The method of claim 6 wherein the biological specimen is whole blood, sputum, serum, plasma, cerebrospinal fluid or urine.

8. The method of claim 6 wherein the presence of the complex is determined by an immunoassay.

9. The method of claim 6 wherein the polypeptide is immobilized on a solid support.

10. The method of claim 2 wherein the biological specimen is whole blood, sputum, serum, plasma, cerebrospinal fluid or urine.

11. The method of claim 2 wherein the presence of the complex is determined by an immunoassay.

12. The method of claim 2 wherein the polypeptide is immobilized on a solid support.

13. A method of diagnosing a hazelnut allergy characterized by a hazelnut-induced systemic reaction comprising: recombinantly producing a polypeptide that forms a complex with serum IgE from a human with said allergy, wherein said polypeptide is encoded by a first nucleic acid having the sequence of nucleotides 25-924 of SEQ ID NO:1 or a second nucleic acid that hybridizes with over the full length of the complement of said first nucleic acid under high stringency conditions comprising 68° C. in aqueous buffered solution and wherein said second nucleic acid encodes a polypeptide that is recognized by antibodies specific for the polypeptide encoded by said first nucleic acid; contacting an IgE-containing biological specimen of a human with said polypeptide; determining the presence or absence of a complex between IgE in the specimen and said polypeptide; and diagnosing hazelnut allergy characterized by a hazelnut-induced systemic reaction if the complex is present.

14. The method of claim 13 wherein the biological specimen is whole blood, sputum, serum, plasma, cerebrospinal fluid or urine.

15. The method of claim 13 wherein the presence of the complex is determined by an immunoassay.

16. The method of claim 13 wherein the polypeptide is immobilized on a solid support.

\* \* \* \* \*

SEQUENCE LISTING

```
<160> NUMBER OF SEQ ID NOS: 10

<210> SEQ ID NO 1
<211> LENGTH: 1767
<212> TYPE: DNA
<213> ORGANISM: Corylus avellana

<400> SEQUENCE: 1
aaacaacatc agatatatat taccatggcc aaacttatct tggtctcttt ttctctgtgc      60
cttcttgtgc tcttcaatgg ctgcctgggt atcaatgtag gactaaggcg gcagcaacag     120
cgatattttg gcgagtgcaa cctcgacagg ctcaatgccc ttgaacccac aaaccgcatc     180
gaggctgaag cttgccagat cgagtcttgg gaccacaacg accagcaatt ccagtgcgct     240
ggggttgccg tcatccggcg aaccattgag cccaatggcc ttctcttgcc ccaatacagc     300
aatgctccag aactcatata cattgagaga ggtaggggaa tcaccggggt cctgtttcct     360
gggtgtcccg aaacatttga agatcctcaa caacaatctc aacagggaca gagacaggga     420
cagggacaga gccagaggtc tgaacaagac cggcatcaga agattcgaca cttccgagag     480
ggagacatca tcgcattgcc agctggagta gcccattggt gctataacga cggtgactcc     540
ccagttgtca cagtctctct ccttcacacc aacaactatg ctaaccagct tgacgagaac     600
cctagacact tctaccttgc cgggaaccca gacgacgagc atcagcgaca gggtcagcag     660
caattcgggc agcgtcgccg ccagcaacag catagccatg tgagcaagg cgagcaagag     720 cagcagggcg aaggaaacaa cgtattcagt ggcttcgatg ctgagttttt ggcggacgcg     780
ttcaacgtgg atgttgacac ggccagaagg cttcagagca accaagacaa aaggaggaac     840
atcgtcaaag tggaaggcag gcttcaggtg gtgaggccgg aaaggtcgcg tcaggaatgg     900
```

-continued

```
gagcgacagg agagacaaga gagggagagt gagcaagagc gggaacgcca gcgtcgccag    960
ggaggacgtg gacgtgatgt caatggcttt gaggagacaa tatgcagctt gaggctcagg   1020
gaaaacatct gcacccgctc acgcgctgac atttacaccg aacaagtcgg tcgcatcaac   1080
accgtcaaca gcaacaccct cccagtcctc cgctggctcc agctcagcgc tgagagagga   1140
gatcttcaaa gggagggtct atatgtaccg cactggaacc tcaatgccca cagtgtggtg   1200
tatgccatac ggggtcgcgc ccgagttcag gtggtggacg acaacggtaa caccgtgttc   1260
gacgatgaac ttagacaggg tcaggtgttg accatccccc agaacttcgc ggtggcgaaa   1320
cgggcagaga gcgagggttt cgagtgggtg gccttcaaga ccaacgacaa cgcccaaatt   1380
agtcctcttg ccggacgaac ctcagccatc agggccttgc cggacgatgt ccttgccaac   1440
gcgtttcaga tttcaaggga ggaagccagg aggctgaaat acaacaggca ggagaccacc   1500
ttggttcgct caagcaggtc ttcatctgag aggaagagga ggtctgagtc tgagggcaga   1560
gctgaagctt aattgaagat caaaaaatgc taatgtaatg cggcacgtag ttttattttg   1620
tggttgctaa gcttagggtt tagggccatc actatgcaac agtccttcct aactagtata   1680
atctgagtgt aaaatacgc acaagggcaa cctttactac aaagaataaa agtgaccgct   1740
ttttctaaaa aaaaaaaaaa aaaaaaa                                        1767
```

<210> SEQ ID NO 2
<211> LENGTH: 515
<212> TYPE: PRT
<213> ORGANISM: Corylus avellana

<400> SEQUENCE: 2

```
Met Ala Lys Leu Ile Leu Val Ser Phe Ser Leu Cys Leu Leu Val Leu
1               5                  10                  15

Phe Asn Gly Cys Leu Gly Ile Asn Val Gly Leu Arg Arg Gln Gln Gln
            20                  25                  30

Arg Tyr Phe Gly Glu Cys Asn Leu Asp Arg Leu Asn Ala Leu Glu Pro
        35                  40                  45

Thr Asn Arg Ile Glu Ala Glu Ala Cys Gln Ile Glu Ser Trp Asp His
    50                  55                  60

Asn Asp Gln Gln Phe Gln Cys Ala Gly Val Ala Val Ile Arg Arg Thr
65                  70                  75                  80

Ile Glu Pro Asn Gly Leu Leu Leu Pro Gln Tyr Ser Asn Ala Pro Glu
                85                  90                  95

Leu Ile Tyr Ile Glu Arg Gly Arg Gly Ile Thr Gly Val Leu Phe Pro
            100                 105                 110

Gly Cys Pro Glu Thr Phe Glu Asp Pro Gln Gln Gln Ser Gln Gln Gly
        115                 120                 125

Gln Arg Gln Gly Gln Gly Gln Ser Gln Arg Ser Glu Gln Asp Arg His
    130                 135                 140

Gln Lys Ile Arg His Phe Arg Glu Gly Asp Ile Ile Ala Leu Pro Ala
145                 150                 155                 160

Gly Val Ala His Trp Cys Tyr Asn Asp Gly Asp Ser Pro Val Val Thr
                165                 170                 175

Val Ser Leu Leu His Thr Asn Asn Tyr Ala Asn Gln Leu Asp Glu Asn
            180                 185                 190

Pro Arg His Phe Tyr Leu Ala Gly Asn Pro Asp Asp Glu His Gln Arg
        195                 200                 205

Gln Gly Gln Gln Gln Phe Gly Gln Arg Arg Gln Gln Gln His Ser
    210                 215                 220
```

```
His Gly Glu Gln Gly Glu Gln Glu Gln Gly Gly Asn Asn Val
225                 230                 235                 240

Phe Ser Gly Phe Asp Ala Glu Phe Leu Ala Asp Ala Phe Asn Val Asp
            245                 250                 255

Val Asp Thr Ala Arg Arg Leu Gln Ser Asn Gln Asp Lys Arg Arg Asn
        260                 265                 270

Ile Val Lys Val Glu Gly Arg Leu Gln Val Val Arg Pro Glu Arg Ser
    275                 280                 285

Arg Gln Glu Trp Glu Arg Gln Glu Arg Gln Glu Arg Glu Ser Glu Gln
290                 295                 300

Glu Arg Glu Arg Gln Arg Arg Gln Gly Gly Arg Gly Arg Asp Val Asn
305                 310                 315                 320

Gly Phe Glu Glu Thr Ile Cys Ser Leu Arg Leu Arg Glu Asn Ile Cys
            325                 330                 335

Thr Arg Ser Arg Ala Asp Ile Tyr Thr Glu Gln Val Gly Arg Ile Asn
        340                 345                 350

Thr Val Asn Ser Asn Thr Leu Pro Val Leu Arg Trp Leu Gln Leu Ser
    355                 360                 365

Ala Glu Arg Gly Asp Leu Gln Arg Glu Gly Leu Tyr Val Pro His Trp
370                 375                 380

Asn Leu Asn Ala His Ser Val Val Tyr Ala Ile Arg Gly Arg Ala Arg
385                 390                 395                 400

Val Gln Val Val Asp Asp Asn Gly Asn Thr Val Phe Asp Asp Glu Leu
            405                 410                 415

Arg Gln Gly Gln Val Leu Thr Ile Pro Gln Asn Phe Ala Val Ala Lys
        420                 425                 430

Arg Ala Glu Ser Glu Gly Phe Glu Trp Val Ala Phe Lys Thr Asn Asp
    435                 440                 445

Asn Ala Gln Ile Ser Pro Leu Ala Gly Arg Thr Ser Ala Ile Arg Ala
450                 455                 460

Leu Pro Asp Asp Val Leu Ala Asn Ala Phe Gln Ile Ser Arg Glu Glu
465                 470                 475                 480

Ala Arg Arg Leu Lys Tyr Asn Arg Gln Glu Thr Thr Leu Val Arg Ser
            485                 490                 495

Ser Arg Ser Ser Glu Arg Lys Arg Arg Ser Glu Ser Glu Gly Arg
        500                 505                 510

Ala Glu Ala
        515

<210> SEQ ID NO 3
<211> LENGTH: 15
<212> TYPE: PRT
<213> ORGANISM: Corylus avellana

<400> SEQUENCE: 3

Asn Asn Val Phe Ser Gly Phe Asp Ala Glu Phe Leu Ala Asp Ala
1               5                   10                  15

<210> SEQ ID NO 4
<211> LENGTH: 30
<212> TYPE: PRT
<213> ORGANISM: Corylus avellana

<400> SEQUENCE: 4

Cys Ala Gly Ala Gly Gly Ile Cys Ala Gly Ala Cys Ala Gly Ala Cys
1               5                   10                  15

Ala Gly Ala Thr Thr Cys Thr Gly Gly Ile Cys Ala Gly Ala
```

```
                    20             25             30

<210> SEQ ID NO 5
<211> LENGTH: 26
<212> TYPE: PRT
<213> ORGANISM: Corylus avellana

<400> SEQUENCE: 5

Cys Ala Cys Thr Thr Cys Thr Ala Cys Cys Thr Ile Gly Cys Thr Cys
1               5                   10                  15

Gly Gly Ile Ala Ala Cys Cys Cys Ala Thr
            20                  25

<210> SEQ ID NO 6
<211> LENGTH: 20
<212> TYPE: DNA
<213> ORGANISM: Corylus avellana

<400> SEQUENCE: 6
atgaggccac ctccgttatc                                          20

<210> SEQ ID NO 7
<211> LENGTH: 20
<212> TYPE: DNA
<213> ORGANISM: Corylus avellana

<400> SEQUENCE: 7
ggaggaggat ccatcttgaa                                          20

<210> SEQ ID NO 8
<211> LENGTH: 9
<212> TYPE: PRT
<213> ORGANISM: Corylus avellana

<400> SEQUENCE: 8

Gln Gly Gln Gln Gln Phe Gly Gln Arg
1               5

<210> SEQ ID NO 9
<211> LENGTH: 14
<212> TYPE: PRT
<213> ORGANISM: Corylus avellana

<400> SEQUENCE: 9

His Phe Tyr Leu Ala Gly Asn Pro Asp Asp Glu His Gln Arg
1               5                   10

<210> SEQ ID NO 10
<211> LENGTH: 15
<212> TYPE: PRT
<213> ORGANISM: Arachis hypogaea

<400> SEQUENCE: 10

Gly Asn Ile Phe Ser Gly Phe Thr Pro Glu Phe Leu Glu Gln Ala
1               5                   10                  15
```